(12) United States Patent
Miller, II et al.

(10) Patent No.: US 8,449,907 B2
(45) Date of Patent: *May 28, 2013

(54) FENTANYL SUSPENSION-BASED SILICONE ADHESIVE FORMULATIONS AND DEVICES FOR TRANSDERMAL DELIVERY OF FENTANYL

(75) Inventors: Kenneth J. Miller, II, St. Albans, VT (US); Sharad K. Govil, Essex, VT (US); Kuljit Singh Bhatia, Scottsdale, AZ (US)

(73) Assignee: Mylan Pharmaceuticals, Inc., Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/192,178

(22) Filed: Jul. 27, 2011

(65) Prior Publication Data

US 2012/0145320 A1 Jun. 14, 2012

Related U.S. Application Data

(63) Continuation of application No. 11/743,411, filed on May 2, 2007, which is a continuation of application No. 11/438,391, filed on May 23, 2006, now abandoned, which is a continuation of application No. 10/283,355, filed on Oct. 30, 2002, now abandoned.

(51) Int. Cl.
*A61F 13/02* (2006.01)
*A61F 13/00* (2006.01)
*A61L 15/16* (2006.01)
*A61K 9/70* (2006.01)

(52) U.S. Cl.
USPC .......................................... 424/448; 424/449

(58) Field of Classification Search
None
See application file for complete search history.

(56) References Cited

U.S. PATENT DOCUMENTS

| | | |
|---|---|---|
| 4,466,953 A | 8/1984 | Keith et al. |
| 4,470,962 A | 9/1984 | Keith et al. |
| 4,588,580 A | 5/1986 | Gale et al. |
| 4,626,539 A | 12/1986 | Aungst et al. |
| 4,655,767 A | 4/1987 | Woodard et al. |
| 4,769,028 A | 9/1988 | Hoffmann et al. |
| 4,839,174 A | 6/1989 | Baker et al. |
| 4,882,377 A | 11/1989 | Sweet et al. |
| 4,906,463 A | 3/1990 | Cleary et al. |
| 4,908,213 A | 3/1990 | Govil et al. |
| 4,938,759 A | 7/1990 | Enscore et al. |
| 4,943,435 A | 7/1990 | Baker et al. |
| 5,006,342 A | 4/1991 | Cleary et al. |

(Continued)

FOREIGN PATENT DOCUMENTS

| | | |
|---|---|---|
| EP | 0622075 A1 | 11/1994 |
| EP | 0913158 A1 | 5/1999 |

(Continued)

OTHER PUBLICATIONS

"Material Safety Data Sheet", Dow Corning® BIO-PSA.*

(Continued)

*Primary Examiner* — Isis Ghali
(74) *Attorney, Agent, or Firm* — McDermott Will & Emery

(57) ABSTRACT

Silicone adhesive formulations are provided, in which fentanyl particles are suspended one or more a solvated silicone adhesives. The formulations can be used for manufacturing improved, matrix-type transdermal devices for administering fentanyl.

1 Claim, 7 Drawing Sheets

U.S. PATENT DOCUMENTS

| | | | |
|---|---|---|---|
| 5,154,929 A | 10/1992 | Shibata et al. |
| 5,186,939 A | 2/1993 | Cleary et al. |
| 5,230,898 A | 7/1993 | Horstmann et al. |
| 5,232,702 A | 8/1993 | Pfister et al. |
| 5,310,559 A | 5/1994 | Shah et al. |
| 5,374,429 A | 12/1994 | Kinoshita et al. |
| 5,474,783 A | 12/1995 | Miranda et al. |
| 5,556,636 A | 9/1996 | Yano et al. |
| 5,603,947 A | 2/1997 | Wong et al. |
| 5,629,014 A | 5/1997 | Kwiatek et al. |
| 5,656,286 A | 8/1997 | Miranda et al. |
| 5,762,952 A | 6/1998 | Barnhart et al. |
| 5,906,830 A | 5/1999 | Farinas et al. |
| 5,928,666 A | 7/1999 | Farinas et al. |
| 5,948,433 A | 9/1999 | Burton et al. |
| 5,958,446 A | 9/1999 | Miranda et al. |
| 5,985,317 A | 11/1999 | Venkateshwaran et al. |
| 5,993,849 A | 11/1999 | Assmus et al. |
| 6,010,715 A | 1/2000 | Wick et al. |
| 6,024,976 A | 2/2000 | Miranda et al. |
| 6,063,399 A | 5/2000 | Assmus et al. |
| 6,139,866 A | 10/2000 | Chono et al. |
| 6,440,454 B1 | 8/2002 | Santoro et al. |
| 6,893,655 B2 | 5/2005 | Flanigan et al. |
| 6,899,894 B1 | 5/2005 | Klein et al. |
| 7,018,648 B2 | 3/2006 | Sournac et al. |
| 7,556,823 B2 | 7/2009 | Miller, II et al. |
| 2001/0033858 A1 | 10/2001 | Zhang |
| 2002/0119187 A1 | 8/2002 | Cantor et al. |
| 2003/0026829 A1 | 2/2003 | Venkatraman et al. |
| 2003/0060479 A1 | 3/2003 | Brown et al. |

FOREIGN PATENT DOCUMENTS

| | | |
|---|---|---|
| EP | 1381352 A1 | 1/2004 |
| JP | 6137725 A | 5/1994 |
| WO | 9640085 A2 | 12/1996 |
| WO | 0033812 A2 | 6/2000 |
| WO | 0126705 A2 | 4/2001 |
| WO | 03018071 A1 | 3/2003 |
| WO | 03018075 A2 | 3/2003 |

OTHER PUBLICATIONS

Product Information, Dow Corning® BIO-PSA.*

Cho, Bee Ah, "Solubility and Crystallization of Fentanyl in Polyisobutylene Films: Parameters that Control the Stability of a Drug in Adhesive System," Dissertation Abstracts International, Apr. 2002, 62(10):4557-B.

Roy, S.D., et al., "Controlled Transdermal Delivery of Fentanyl: Characterizations of Pressure-Sensitive Adhesives for Matrix Patch Design" Journal of Pharmaceutical Sciences, 1996, vol. 85, No. 5, pp. 491-495.

Roy, S.D., et al., "Transdermal Delivery of Narcotic Analgesics: Comparative Metabolism and Permeability of Human Cadaver Skin and Hairless Mouse Skin" Journal of Pharmaceutical Sciences, 1994, vol. 83, No. 12, pp. 1723-1728.

Roy, S.D., et al., "Transdermal Delivery of Narcotic Analgesics: Comparative Permeabilities Narcotic Analgesics Through Human Cadaver Skin" Pharmaceutical Research, 1989, vol. 6, No. 10, pp. 825-832.

Roy, S.D., et al., "Transdermal Delivery of Narcotic Analgesics: pH, Anatomical, and Subject Influences on Cutaneous Permeability of Fentanyl and Sufentanil" Pharmaceutical Research, 1990, vol. 7, No. 8, pp. 842-847.

Van Buskirk, G.A. e al., "Scale-up of Adhesive Transdermal Drug Delivery Systems" Pharmaceutical Research, 1997, vol. 14, No. 7, pp. 848-852.

Approved Judgement of the Hourable Mr Justice Kitchin Dated Feb. 12, 2009 for Case No. HC07 C0222.

Richard J. Lewis: "Hawley's Condensed Chemical Dictionary", 14th Edition, 2001 p. 415 and 1062.

Schechter, Neil L., M.D., et al., "Pain in Infants, Children, and Adolescents"; Second Edition, Copyright 2003, publisher Lippincott Williams & Wilkins: Section II, "Therapeutic Interventions", "Fentanyl(s)", pp. 196-198.

Twersky et al. "Hemodynamics and Emergency Profile of Remifentanil Versus Fentanyl Prospectively Compared in a Large Population of Surgical Patients", Journal of Clinical Anesthesia, 2001.

Japanese Application No. 2004-550226: Official Action from the Japanese Patent Office from May 2010, in English with cited references JP61-37725A in Japanese which corresponds with U.S. Patent No. 4,588,580.

Declaration under 37 CFR 1.131 with Exhibits A and B, executed by attorney Lydia G. Olsen, USPTO Reg. No. 48, 487, dated Apr. 22, 2009, filed in USPTO on Apr. 22, 2009 in U.S. Appl. No. 12/260,050 which has common inventor Kenneth J. Miller II and common owner Mylan Laboratories.

Declaration under 37 CFR 1.132 with Exhibits 1, 2, and 3, executed by inventor Kenneth J. Miller II, dated Apr. 22, 2009, filed in USPTO on Apr. 22, 2009 in U.S. Appl. No. 12/260,050 which has common inventor Kenneth J. Miller II and common owner Mylan Laboratories.

Notice of Allowance dated May 26, 2009 in U.S. Appl. No. 12/260,050 which has common inventor Kenneth J. Miller II and common owner Mylan Laboratories.

U.S. Appl. No. 11/743,411: Final Office Action dated Dec. 20, 2010, including PTO 892 and references cited therein.

Yu et al.: "Transdermal Fentanyl Matrix Patch—Evaluation of a Parallel Binary Matrix System" by Samyang Corporation, Conference Poster 2000.

Yu et al.: "Millenial World Congress of Pharmaceutical Sciences Abstracts" Moscone Center, San Francisco, California, Apr. 16-20, 2000.

* cited by examiner

FENTANYL SUSPENSION-BASED SILICONE ADHESIVE FORMULATIONS AND DEVICES FOR TRANSDERMAL DELIVERY OF FENTANYL

RELATED APPLICATIONS

This application is a continuation of application No. 11/743,411, filed May 2, 2007, which is a continuation of application No. 11/438,391, filed May 23, 2006 (abandoned), which is a continuation of application No. 10/283,355, filed Oct. 30, 2002 (abandoned). The contents of these applications are hereby incorporated by reference in their entirety.

FIELD OF THE INVENTION

The present invention relates generally to the field of transdermal drug delivery. More particularly, the present invention relates to fentanyl suspension-based, silicone pressure sensitive adhesive formulations and their use in making devices for improved transdermal delivery of fentanyl.

BACKGROUND OF THE INVENTION

A pressure sensitive adhesive is a material that adheres to a surface with slight pressure and releases from the surface with negligible transfer of the adhesive to the surface. Silicone pressure sensitive adhesives in particular have been used for transdermal drug delivery, which involves administering a drug by adhering a drug-containing device or patch to a patient's skin.

One type of transdermal patch is a polymer matrix or monolithic device in which the active agent is contained in a polymer matrix film through which the active agent diffuses to the skin. Such patches are preferred because they are relatively simpler to manufacture and more comfortable to wear compared to reservoir-type devices. Transdermal patches having a monolithic polymer film layer in which the active agent is contained are disclosed in U.S. Pat. No. 4,839,174, as well as in U.S. Pat. Nos. 4,908,213 and 4,943,435.

Fentanyl is an opioid analgesic which, in clinical settings, exerts its principle pharmacologic effects on the central nervous system. Its primary actions of therapeutic value are analgesia and sedation, and it is indicated for the management of chronic pain in patients who require opioid analgesia for pain that is typically unmanageable by lesser means. In particular, fentanyl is used clinically for the relief of acute post-operative and chronic cancer pain.

Transdermal patches containing silicone pressure sensitive adhesive compositions are described in U.S. Pat. No. 5,232,702 (Pfister et al.), WO 00/33812 (Miranda et al.), WO 96/40085 (Mantelle et al.), and U.S. Pat. No. 5,603,947, all fully incorporated herein by reference.

U.S. Pat. No. 5,232,702 describes silicone pressure sensitive adhesives containing (i) a silicone fluid, (ii) a silicate resin, and (iii) a cohesive strengthening agent. In one embodiment, the pressure sensitive adhesive includes a high molecular weight polydimethylsiloxane as the silicone fluid. Organic solvents disclosed as suitable for dissolving the silicone fluid and the silicate resin include aromatics such as toluene and xylene; aliphatics such as heptane and hexane; chlorinated solvents such as 1,1,1-trichloroethane and trichlorotrifluoroethane; fluorocarbons such as Freon 113; aliphatic esters such as ethyl acetate; and mixtures thereof. Example D describes how transdermal adhesive matrix-type patches were prepared containing 17-beta estradiol, a skin penetration enhancer (PGML), a high silanol containing silicone pressure sensitive adhesive, and calcium stearate as the cohesive strengthening agent. Two different high silanol containing adhesives were used, both of which were prepared in a xylene solvent by homogenously mixing a silicate resin, xylene, and a silicone fluid. The mixture was then heated, stripped of non-volatile content, and eventually redissolved in hexane to a non-volatile content of 50 wt %. The final 17-beta estradiol-containing adhesive solution was cast onto a polyester release liner, allowed to air dry, and then laminated onto a polyester backing film.

WO 00/33812 describes a transdermal patch for administering a volatile liquid drug, such as nicotine. The transdermal patch contains a backing layer, a pressure sensitive silicone adhesive layer and a pressure sensitive acrylic adhesive layer containing the drug, and a removable release liner layer. The silicone adhesive layer is prepared by dissolving a silicone adhesive in hexane. WO 00/33812 reports (at p. 6) that other solvents, such as heptane and toluene, are not suitable because they require higher processing temperatures and thus result in more drug degradation and/or evaporation during coating and drying.

WO 96/40085 describes transdermal matrix patches for administering drugs, such as selegiline, nitroglycerin and nicotine, which are liquid at normal room temperature. WO 96/40085 suggests making a monolithic matrix of the drug in an adhesive by mixing one or more polymeric adhesives, preferably polyacrylate and polysiloxane, and the drug in a volatile solvent, casting the mixture, and evaporating the solvent. Examples of volatile solvents provided are isopropanol, ethanol, xylene, toluene, hexane, cyclohexane, heptane, ethyl acetate and butyl acetate.

Similarly, U.S. Pat. No. 5,603,947 describes in Example 1 the use of heptane to cast a silicone adhesive layer in nicotine patches.

In both of the above references, the drugs are dissolved in the silicone adhesives prior to casting.

Transdermal patches containing fentanyl in a silicone pressure sensitive adhesive are also known in the art, as described, for example, in U.S. Pat. Nos. 4,588,580 (Gale et al.) and 5,186,939 (Cleary et al.), also fully incorporated herein by reference.

U.S. Pat. No. 4,588,580 describes in Example 6 a fentanyl-containing monolithic patch that was made using Dow Corning amine resistant silicone adhesive and silicone medical fluid having 10 and 20 percent fentanyl base dispersed therein.

U.S. Pat. No. 5,186,939 describes a laminated composite for administering fentanyl transdermally, including an adhesive-drug reservoir layer comprising fentanyl dissolved in an amine-resistant polydimethylsiloxane. Example 1 describes that a fentanyl-containing pressure sensitive adhesive composition was prepared consisting of 1.8% fentanyl base, 4% permeation enhancer (PGML), 2.0% silicone oil (Dow Corning Medical Fluid) and 92.5% amine resistant polydimethylsiloxane (Dow Corning X7-2900) dissolved in trichlorotrifluoroethane (freon) to provide a 50% solution.

In addition, a fentanyl-containing, reservoir-type transdermal patch as approved by the FDA is described in the 2002 Physician's Desk Reference. Duragesic® is a rectangular transparent patch comprising a protective liner and four functional layers. Proceeding from the outer surface toward the surface adhering to the skin, these layers are: 1) a backing layer of polyester film; 2) a drug reservoir of fentanyl and alcohol USP gelled with hydroxyethyl cellulose; 3) an ethylene-vinyl acetate copolymer membrane that controls the rate of fentanyl delivery to the skin surface; and 4) a fentanyl containing silicone adhesive.

The present invention is believed to offer improvements and advantages over prior fentanyl-containing transdermal devices.

SUMMARY OF THE INVENTION

One aspect of the invention is a fentanyl-containing, silicone pressure sensitive adhesive formulation comprising a blend of fentanyl suspended in a solvated silicone pressure sensitive adhesive. The selected solvent is one that can substantially or fully solvate or dissolve the adhesive while keeping the fentanyl suspended in the solvated adhesive.

The formulation of the invention can be made by blending fentanyl particles directly with one or more solvated silicone adhesives to form a suspension of fentanyl particles in the solvated adhesive(s). Alternatively, the formulation can be made by first combining the fentanyl particles with a silicone fluid to wet the particles and form a slurry, which slurry then can be blended with the solvated silicone adhesive(s) to also form a suspension of fentanyl particles in the solvated adhesive(s).

The above formulations are useful for making monolithic devices for improved transdermal administration of fentanyl.

Thus, another aspect of the invention is a method for making a laminate, which is useful for making a monolithic patch for transdermal administration of fentanyl. The method comprises the steps of:

a) selecting a solvent that can substantially or fully solvate a silicone adhesive while keeping fentanyl particles, when blended with the solvated adhesive, suspended in the solvated adhesive;

b) blending fentanyl particles with one or more silicone adhesives which are solvated with the above solvent, to form a blend formulation in which fentanyl particles are suspended in the solvated adhesives;

c) casting the blend formulation onto a support material; and d) removing the solvent, to produce a laminate containing the support material and a fentanyl suspension-containing adhesive layer.

In a preferred embodiment, the blend formulation formed in step (b) is further treated prior to the casting step.

The blend formulation preferably is cast onto a backing layer or release liner. The solvent can be removed during drying by evaporation from the adhesive layer. The laminate can be further processed to produce a monolithic device containing a backing layer, fentanyl suspension-containing adhesive layer, and release liner.

A further aspect of the invention then is a monolithic patch for administering fentanyl transdermally to an individual comprising:

(a) a backing layer substantially impervious to the fentanyl to be administered transdermally;

(b) a fentanyl-containing adhesive layer in contact with at least a portion of the backing layer, the adhesive layer being cast from a formulation comprising a blend of fentanyl particles suspended in one or more solvated silicone adhesives; and (c) a removable release liner in contact with the adhesive layer.

A still further aspect of the invention is a method for administering fentanyl transdermally to an individual in need of such administration, comprising applying to the skin of the individual a monolithic patch comprising:

(a) a backing layer substantially impervious to the fentanyl to be administered transdermally; and (b) a fentanyl-containing adhesive layer in contact with the backing layer, the adhesive layer being cast from a formulation comprising a blend of fentanyl particles suspended in one or more solvated silicone adhesives.

In a preferred embodiment, the selected solvent is heptane.

An adhesive layer according to the present invention was found to provide improved transdermal release of fentanyl, as well as improved adhesion of transdermal devices to skin. Also with the present invention, greater amounts of fentanyl can be delivered from the patch than from solution-based matrix patches, thus leaving lower residual amounts of fentanyl in the patch after administration.

The present invention provides non-invasive sustained analgesia for periods ranging from 24 hours to 168 hours, and preferably for 72 hours to 84 hours (about 3 to 3½ days) or 72 hours to 168 hours (about 3 to 7 days). Preferred embodiments of the invention include 3 day (72 hours) and 7 day (168 hours) patches.

Clinical lot-F1BJ10001 (Suspension Blend: 4% Fentanyl, 8.6% 360 Medical Fluid);

Duragesic 100 µg/hr Lot 8910192;

246p110C (Solution Blend, Recrystallized Laminate: 4% Fentanyl, 6.5% 360 Medical Fluid.

Figure 3:
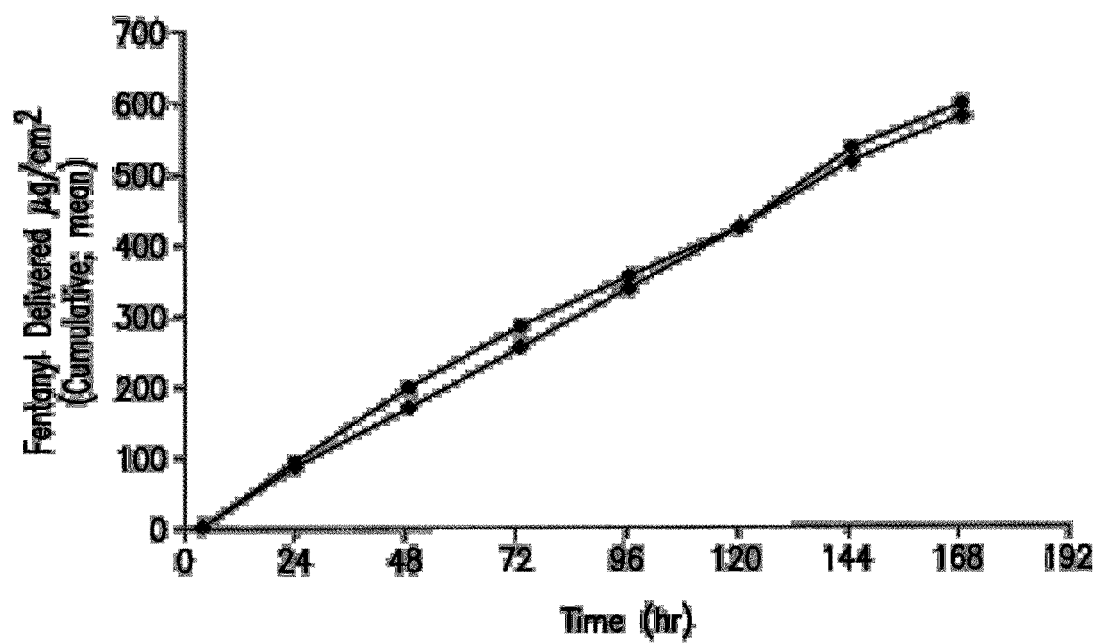

FIG. 3 is a graph comparing in vitro transdermal delivery rates of fentanyl for a 7-day suspension blend-based recrystallized device (3 Donors, 6 Chambers/Donor).

246p114A (Suspension Blend: 9.5% Fentanyl, 6.6% 980 Medical Fluid);

246p118A (Solution Blend, Recrystallized Laminate: 9.5% Fentanyl, 6.5% 360 Medical Fluid).

Figure 4:
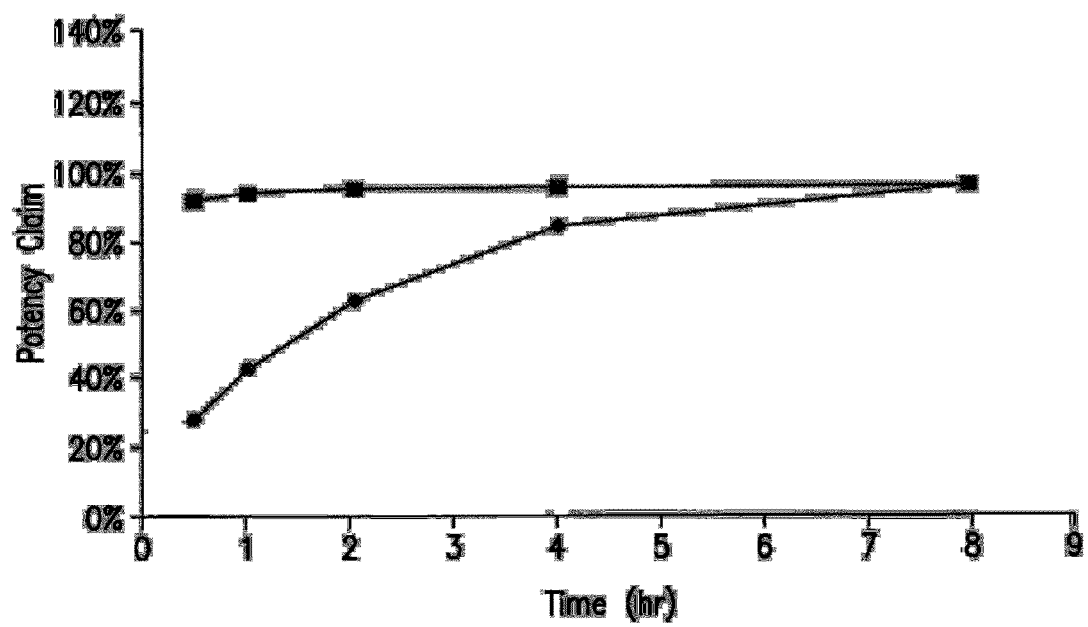

FIG. 4 is a graph comparing release rates of fentanyl for a 3-day suspension blend-based device of the invention and a 3-day solution blend-based recrystallized device.

246P11OC (Solution Blend, Recrystallized Laminate: 4% Fentanyl, 6.5% 360 Medical Fluid).

Clinical lot F1BJ0001 (Suspension Blend: 4% Fentanyl, 8.5% 360 Medical Fluid).

Figure 5:
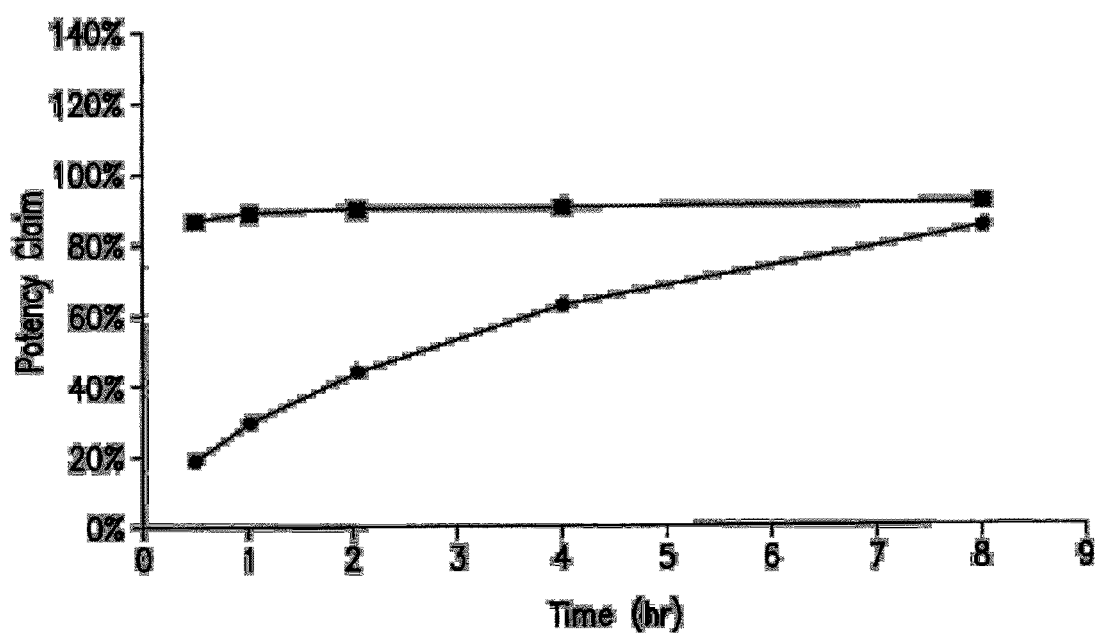

FIG. 5 is a graph comparing release rates of fentanyl for a 7-day suspension blend-based device of the invention and a 7-day solution blend-based recrystallized device.

246p114A (Solution Blend: 9.5% Fentanyl, 8.5% 360 Medical Fluid);

246p118A (Solution Blend, Recrystallized Laminate: 9.5% Fentanyl, 6.5% 360 Medical Fluid).

Figure 6:
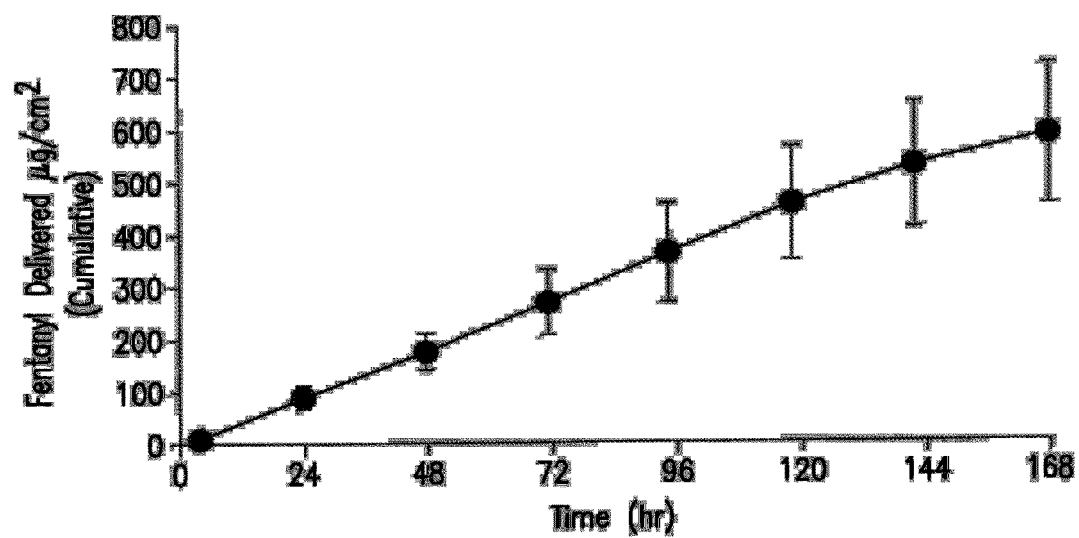

FIG. 6 is a graph showing the in vitro transdermal delivery rate of fentanyl for 7days from a suspension blend-based device of the invention made without silicone fluid (360 Medical Fluid).

Figure 7:
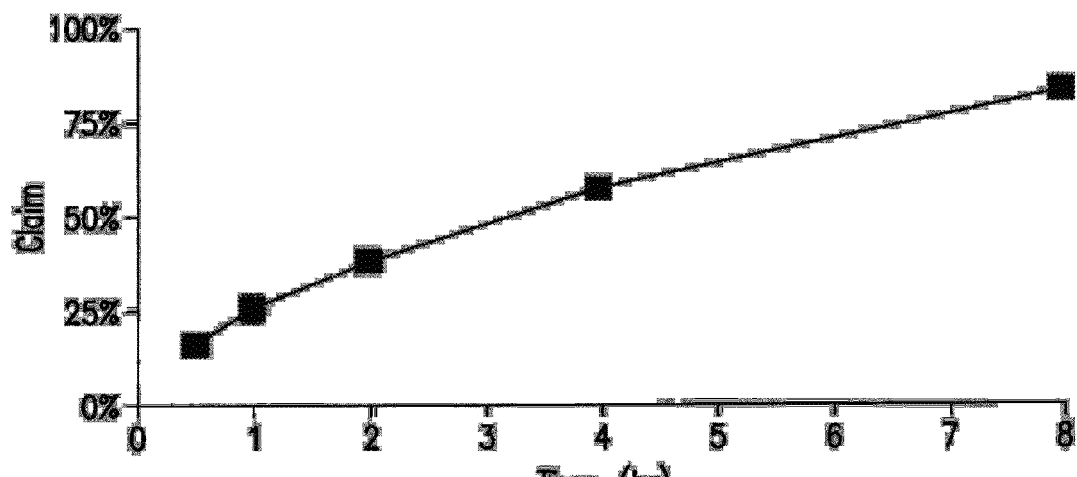

FIG. 7 is a graph showing the in vitro rate of fentanyl release from a suspension blend-based device of the invention made without silicone fluid. (360 Medical Fluid).

DETAILED DESCRIPTION OF THE INVENTION

The present invention provides formulations in which fentanyl particles are suspended in a solvent-based silicone adhesive. The fentanyl suspension is produced by blending fentanyl particles with a solvent-based silicone adhesive. The selected solvent is one that can substantially or fully solvate or dissolve the silicone adhesive. The selected solvent also must be suitable for preventing high concentrations, e.g., greater than about 1.0% w/w (dry weight), of fentanyl particles from dissolving in the solvated adhesive.

The total amount of fentanyl need not be suspended in the solvated adhesive, thus allowing for instances when a portion of the fentanyl is dissolved in the solvated adhesive. In the discussion below, the focus will be on "suspended particles" or "suspensions" of fentanyl, but it is to be understood that this does not exclude those embodiments in which a small proportion of the fentanyl is dissolved in the solvated adhesive.

The solvent preferably is heptane, but also may be selected from other organic solvents, preferably closely related aliphatic solvents such hexane and octane, for example, as long as the selected solvent exhibits the above-described dissolution features.

The formulations made in accordance with the present invention are used to manufacture improved devices for delivering fentanyl transdermally, particularly monolithic transdermal patches. The devices may be manufactured by casting the formulation onto a support material such as a backing layer or release liner to form a fentanyl suspension-containing adhesive layer, which can be further processed to make a transdermal patch for delivering fentanyl.

Thus, to manufacture a device having the advantages of the present invention, one most first produce a formulation comprising a liquid blend of fentanyl particles suspended in a solvated silicone adhesive, which formulation then is subsequently processed to make the device. Alternative methods for producing or achieving a fentanyl suspension-containing adhesive layer according to the invention may be apparent to persons skilled in the art, and these alternative methods thus also fall within the scope of the present invention.

In a preferred embodiment, one or more silicone pressure sensitive adhesives is dissolved in heptane, while fentanyl particles are mixed with a silicone fluid to form a slurry. The slurry of fentanyl in silicone fluid then is blended with a portion of the heptane-solvated silicone adhesive and passed through a high shear colloid mill or other mixing device to form a suspension. This suspension then is blended with the remaining heptane-solvated silicone adhesive to form the final (and more dilute) suspension. The composition then is cast onto a release liner and passed through an oven(s) to drive off the heptane. A backing film then is laminated onto the dried adhesive matrix.

In another preferred embodiment, the device or patch is produced by casting a blend of heptane-solvated adhesive(s) and suspended (solid) fentanyl alkaloid particles. A slurry is produced by mixing fentanyl directly with a portion of the heptane-solvated silicone adhesive(s). No silicone fluid is used. This slurry then is passed through a colloid mill or similar mixing device to form a suspension. This suspension then is blended with the remaining heptane-solvated silicone adhesive(s) to form the final (and more dilute) suspension that can be cast onto a release liner and passed through an oven to drive off the heptane. A backing film then is laminated onto the dried adhesive matrix.

The silicone pressure sensitive adhesive preferably is solvated in about 20% to about 50% heptane, and more preferably in about 30% heptane. In addition to contributing to formation of a fentanyl suspension, other advantages of using heptane include decreased toxicity as compared to other solvents, which include, for example, toluene, xylene and other aromatics generally.

In a preferred embodiment, fentanyl particles are suspended uniformly in the solvated silicone adhesive as small particles, preferably crystalline particles.

In the present invention, it is believed that as fentanyl leaves the system during the course of wear, the suspended drug in the system dissolves and replenishes the delivered drug. The present invention as a result maintains a level thermodynamic activity (driving force) for the drug over long periods of wear. No other type of reservoir is known to have such capability. The present invention thus permits long periods of delivery without requiring that a large excess of fentanyl be present.

Suitable silicone adhesives include pressure sensitive adhesives made from silicone polymer and resin. The polymer to resin ratio can be varied to achieve different levels of tack. Examples of useful silicone adhesives which are commercially available include the standard BioPSA® series (7-4400, 7-4500 and 7-4600 series) and the amine compatible (endcapped) BioPSA® series (7-4100, 7-4200 and 7-4300 series) manufactured by Dow Corning. Preferred heptane-solvated silicone adhesives include BIO-PSA® 7-4201, BIO-PSA® 7-4301, and BIO-PSA® 7-4501.

In one embodiment, in which silicone medical fluid is used, the preferred amount of silicone pressure sensitive adhesive used is from about 75% to about 99% w/w (dry weight), and more preferably from about 80% to about 90% w/w (dry weight).

In another embodiment, in which one or more different silicone adhesives may be used, optionally in the presence of silicone medical fluid, the preferred combined amount of silicone pressure sensitive adhesive is from about 75% to about 99% w/w (dry weight), more preferably from about 85% to about 95% w/w (dry weight), and most preferably about 91% w/w (dry weight).

Preferred silicone fluids include high molecular weight polydimethylsiloxane, Dimethicone NF (Dow 360 Silicone Medical Fluid, 100 cSt and other viscosities). Preferred amounts of silicone fluid are from about 0% w/w to about 25% w/w (dry weight), more preferably from about 2% w/w to about 10% w/w (dry weight), even more preferably from about 5% w/w to about 8.5% w/w (dry weight), and most preferably about 6.5% w/w (dry weight). Preferred viscosities of the silicone fluid are from about 20 cSt to about 350 cSt, and most preferably about 100 cSt.

Alternatives to silicone fluid, such as mineral oil, also may be used and are within the scope of the invention.

Figure 1A:
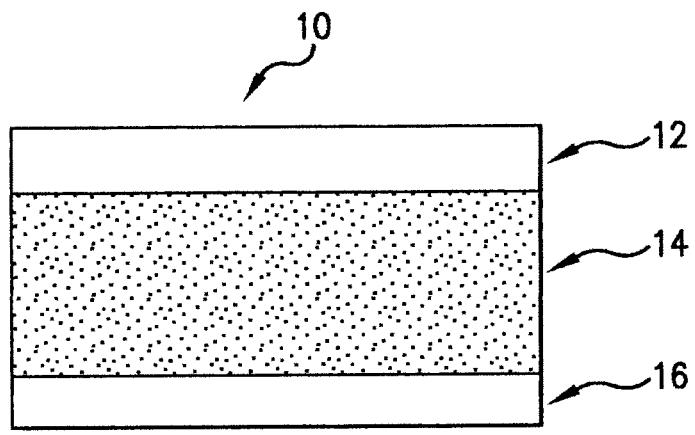
FIG. 1A is a elevational cross-sectional view of an embodiment of a transdermal medical device or patch in accordance with the invention.
Figure 1B:
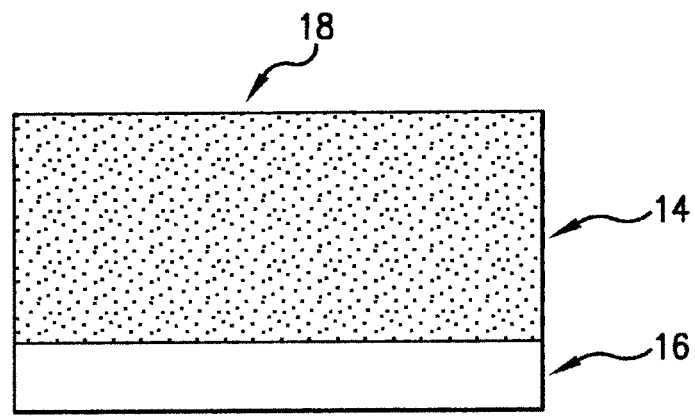
FIG. 1B is a elevational cross-sectional view of an embodiment of a suspension-cast laminate of the invention.

The width or thickness of the adhesive layer (shown as 14 in each of FIGS. 1A and 1B) is that width which provides at least sufficient adhesion of the device to the skin of the host. The width or thickness also may vary depending upon such factors as the amount of drug to be delivered from the composition or adhesive layer and the desired wear period. The thickness of the adhesive layer will usually range from about 10 to 300 µm, more preferably 70 to about 140 µm. Expressed alternatively, the adhesive layer will be present at about 1 to about 30 mg/cm$^2$, more preferably about 7 to about 14 mg/cm$^2$. Variations also can be determined as a matter of routine experimentation by those of ordinary skill in the art. The width also need not be uniform and may vary around the perimeter of the device, e.g., to provide a specific geometric shape or to provide a tab for removal of a protective liner.

Fentanyl is administered preferably in the free base form. Fentanyl alkaloid powder is available from Mallinckrodt. In another embodiment, an analgetically effective relative of fentanyl may be administered, including sufentanil, carfentanil, lofentanil, and afentanil. The quantity of fentanyl contained in the adhesive layer is preferably that quantity sufficient to provide a pharmaceutically or physiologically effective dosage rate of the active agent to a host in need thereof. The quantity of fentanyl also is sufficient to maintain at least a partial suspension of the fentanyl in a solvated adhesive. This quantity can be readily determined by those of ordinary skill in the art without undue experimentation.

In one embodiment, preferred amounts are about 1% to about 10% w/w (dry weight), more preferably about 3% to about 7% w/w (dry weight), and most preferably about 4.0% w/w (dry weight) of fentanyl.

In another embodiment, preferred amounts are about 5% to about 15% w/w (dry weight), more preferably about 8% to about 12% w/w (dry weight), and most preferably about 9.1% w/w (dry weight) of fentanyl.

Preferred delivery rates will usually be in the range of about 5 to about 250 μg/hour, more preferably about 10 mg/hour to about 100 μg/hour, and most preferably about 25, 50, 75 and 100 μg/hour.

A flux enhancer to promote the penetration of the fentanyl through the skin may be included in the adhesive layer. Suitable enhancers include those described in U.S. Pat. No. 4,573,966, including, monovalent, saturated and unsaturated aliphatic and cycloaliphatic alcohols having 6 to 12 carbon atoms such as cyclohexanol, lauryl alcohol and the like; aliphatic and cycloaliphatic hydrocarbons such as mineral oil; cycloaliphatic and aromatic aldehydes and ketones such as cyclohexanone; N,N-di(lower alkyl)acetamides such as N,N-diethyl acetamide, N,N-dimethyl acetamide, N-(2-hydroxyethyl)acetamide, and the like; aliphatic and cycloaliphatic esters such as isopropyl myristate and lauricidin; N,N-di (lower alkyl)sulfoxides such as decylmethyl sulfoxide; essential oils, nitrated aliphatic and cycloaliphatic hydrocarbons such as N-methyl-2-pyrrolidone and azone; salicylates, polyalkylene glycol silicates; aliphatic acids such as oleic acid and Lauric acid, terpenes such as cineole, surfactants such as sodium lauryl sulfate, siloxanes such as hexamethyl siloxane; mixtures of the above materials; and the like.

The backing layer (identified as 12 in each of FIGS. 1A and 1B) is preferably a thin film or sheet. In some instances, because of the area of skin to which the device is to be attached, the device, and therefore the backing layer 12, may be opaque or colored for cosmetic reasons. In one embodiment, it is a clear layer that is occlusive with respect to the active agent or drug, printed matter thereon. The backing layer 12 normally provides support and a protective covering for the device.

The backing layer 12 is preferably made of a material or combination of materials that is preferably impermeable, or at least substantially impermeable, to the adhesive layer and the fentanyl contained therein.

Suitable materials for the backing layer 12 include those known in the art for use with pressure sensitive adhesives. For example, the backing layer 12 can comprise a polyolefin, including polyethylene; a polyester; multi-layer EVA film and polyester; polyurethane; or combinations thereof. A preferred backing material is MEDIFLEX® 1000, a polyolefin manufactured by Mylan Technologies, Inc. Other suitable materials include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidene chloride (e.g., SARAN), ethylene-methacrylate copolymer (Surlyn), paper, cloth, aluminum foil and polymer-metal composites.

The material that forms the backing layer 12 may be flexible or non-flexible. Preferably, a flexible backing layer is employed to conform to the shape of the body member to which the device is attached.

In one embodiment, the medical device (10 in each of FIGS. 1A and 1B) contains a protective release liner (identified as 16 in each of FIGS. 1A and 1B) attached to the device at the surface to be adhered to the skin, namely the fentanyl-containing adhesive layer. The release liner 16 is removed before the device 10 is placed on the skin. The release liner 16 is thus made of a material(s) that permits the liner to be easily stripped or peeled away from the adjacent pressure sensitive adhesive layer. The release liner 16 may be made of the same materials suitable for use in the backing layer 12 as discussed above. Such material is preferably made removable or releasable from the adhesive layer, for example, by conventional treatment with silicon polymers, fluoropolymers (e.g., Teflon) or other suitable coatings on the surface thereof. The removal of the device 10 from the release liner 16 may also be provided by mechanical treatment of the release liner 16, e.g., by embossing the release liner.

Suitable release liners include those known in the art for use with pressure sensitive adhesive compositions. For example, the release liner can comprise a fluorosilicone coated polyester. A preferred release liner is MEDIRELEASE® 2500, manufactured by Mylan Technologies, Inc., or a fluoropolymer-treated polyester, such as Scotchpak® 1022, manufactured by 3M Pharmaceuticals/D.D.S. The release liner 16, however, can comprise various layers, including paper or paper-containing layers or laminates; various thermoplastics, such as extruded polyolefins, such as polyethylene; various polyester films; foil liners; other such layers, including fabric layers, coated or laminated to various polymers, as well as extruded polyethylene, polyethylene terephthalate, various polyamides, and the like.

In one embodiment, the release liner 16 includes a laminate of an outer foil layer and an inner layer of plastic, such as polyethylene or the like, which is rendered releasable not only by means of a siliconized coating, but which also includes an embossed or roughened surface. Embossment is described in U.S. Pat. No. 6,010,715 (Bertek), which is fully incorporated herein by reference.

In one embodiment of this invention, the patch further comprises a fentanyl-free adhesive layer in between the backing layer 12 and the fentanyl-containing adhesive layer 14. This additional adhesive layer extends beyond at least a portion of the fentanyl-containing adhesive layer to provide a further surface area that can adhere to the skin of the wearer, thereby enhancing the adhesive qualities of the device or patch. The size and shape of the backing layer will be essentially co-extensive with the size and shape of this additional adhesive layer. This fentanyl-free adhesive layer can comprise any conventional adhesive, such as a polyisobutylene or an acrylic acid polymer, such as alkyl acrylate or methacrylate polymers, as found in any of a variety of commercially available transdermal patches or tapes.

The compositions of this invention possess sufficient adhesive properties that once the release liner is removed and the composition is applied to the skin the composition can remain in place for a period of time sufficient to distribute the desired amount of the drug contained therein with a low incidence of debonding.

One skilled in the transdermal art would readily recognize the possible sizes of devices or patches in accordance with the invention. The patch sizes preferably vary depending on the desired delivery rates of fentanyl, preferably increasing in size as the desired delivery rate increases. Preferred delivery rates are from about 5 to about 300 μg/hr, more preferably about 50 to about 200 μg/hr, and most preferably about 25, 50, 75 and 100 μg/hour. These delivery rates correspond to patch sizes of 1.25 to about 75 cm$^2$, more preferably about 12.5 to about 50 cm$^2$, and most preferably 6.25, 12.5, 18.75, and 25 cm$^2$, respectively.

The device 10, once formed, may be kept sealed in an air-tight pouch prior to use. The device of the present invention is used in the same manner as those devices which are conventional in the prior art. In particular, the release liner 16 attached to the skin-side surface of the adhesive layer 14 of the device 10 for contact with the skin or mucosa of the host is removed and such surface of the adhesive layer 14 is applied to the desired area of the skin or mucosa.

The host or individual to which an active agent is administered by means of the inventive device may be any host in which fentanyl has the desired effect. The host may be, for example, a mammal such as a human being, or any warm-blooded or cold-blooded animal. The advantage of administering fentanyl may be therapeutic or experimental. The device of this invention may also be used for any other advantageous purpose.

tanyl in 360 Medical Fluid (dimethicone NF) and a portion of the heptane-solvated silicone adhesive were blended and passed through a high shear colloid mill to form a suspension. This suspension was then blended with the remaining heptane-solvated silicone adhesive to form the final (and more dilute) suspension that was cast onto a release liner and passed through ovens to drive off the heptane. The final step in this process was laminating a backing film onto the dried adhesive matrix.

The recrystallized formulation (246P110C) was produced by casting a blend of ethyl acetate-solvated adhesive and dissolved fentanyl alkaloid. In this process, the fentanyl was combined with the 360 Medical Fluid and the ethyl acetate-solvated silicone adhesive. The fentanyl dissolved completely to form a true solution. This solution blend was then cast onto the release liner and dried in an oven, whereupon the fentanyl crystallized. The final step in this process also was laminating the backing film onto the dried adhesive matrix.

Table 4 shows the comparison of the above two formulations tested (which are theoretically identical in their dry form).

TABLE 4

| Lot Number | Description | Adhesive | 360 Medical Fluid (100 cSt) | Fentanyl | Residual Solvent (Trace quantities) |
|---|---|---|---|---|---|
| R6J0001 | Clinical Manufactured 6.25 cm$^2$ 25 μg/hr | 89.5% w/w (7-4201) | 6.5% w/w | 4.0% w/w | Heptane |
| 246P110C | Laboratory Recrystallized Laminate 4% Fentanyl | 89.5% w/w (7-4202) | 6.5% w/w | 4.0% w/w | Ethyl Acetate |

Various embodiments of the present invention were prepared and tested in accordance with testing procedures recognized in the art. In particular, release of fentanyl from recrystallized laminates was compared to fentanyl release from suspension-cast laminates in accordance with the invention.

Four active laminates as described in Table 3 were made and tested for in vitro transdermal delivery, in vitro rate of release, and Polyken probe tack. In addition, the gross nature of the four blends was qualitatively assessed. The results are summarized below.

Formulation Descriptions of Fentanyl from Recrystallized vs. Suspension-Cast Laminates

TABLE 3

| Fentanyl | Blend Solvent | Blend | Lot # |
|---|---|---|---|
| 4.0% w/w | Heptane (30%) | Suspension | R6J0001 |
| 4.0% w/w | Ethyl Acetate (41%) | Solution | 246P110C |
| 9.5% w/w | Heptane (30%) | Suspension | 246P114A |
| 9.5% w/w | Ethyl Acetate (55%) | Solution | 246P118A |

Figure 2:
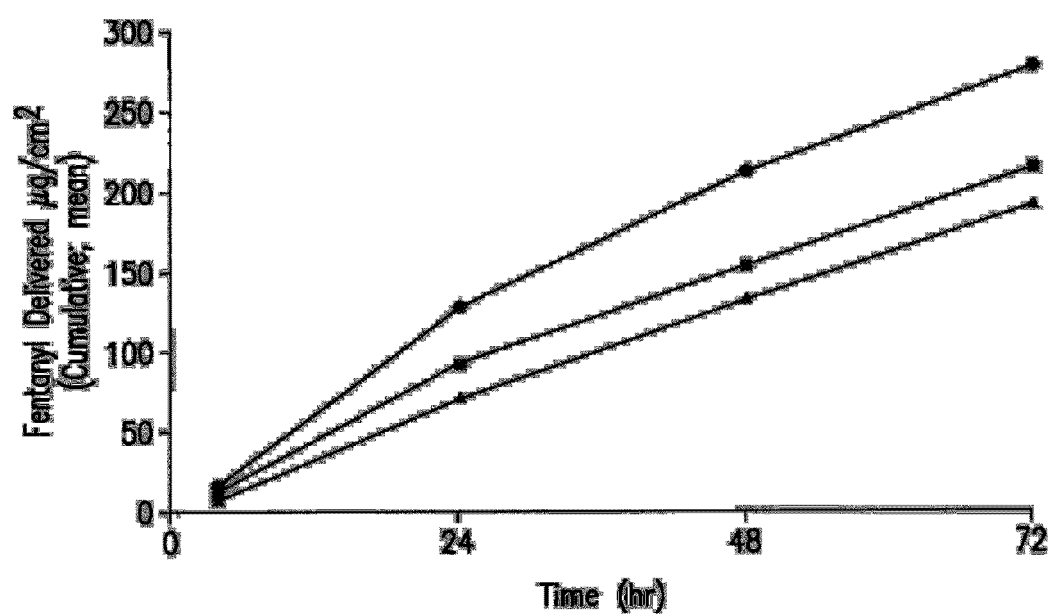
FIG. 2 is a graph comparing in vitro transdermal delivery rates of fentanyl for a 3-day suspension blend-based device of the invention, a 3-day solution blend-based recrystallized device, and a Duragesic transdermal patch (3 Donors, 2 to 6 Chambers per Donor).

In Vitro Transdermal Delivery of Fentanyl from Recrystallized vs. Suspension-Cast Laminates FIG. 2 shows the cumulative in vitro transdermal delivery of fentanyl from laminates identical in content, but produced by different procedures. The lot R6J0001 was produced by casting a blend of heptane-solvated silicone adhesive and suspended (solid) fentanyl alkaloid particles. A slurry of fen- FIG. 2 shows that the 3-day suspension-cast formulation delivered in vitro more fentanyl per unit time than the recrystallized formulation.

Table 5 shows a comparison of the (wet) composition of a suspension blend formulation and the final (dry) composition of an adhesive matrix according to the invention.

TABLE 5

| Component | Wet (w/w) | Dry (w/w) |
|---|---|---|
| Fentanyl | 2.86% | 4.0% |
| Bio-PSA® 7-4201 Silicone Adhesive | 92.49% | 90.5% |
| 360 Medical Fluid (100 cSt) | 4.65% | 6.5% |

FIG. 3 shows the cumulative in vitro transdermal delivery of fentanyl from 7-day patches, also identical in content, but produced by different procedures. Lot 246P114A was produced by casting a blend of heptane-solvated silicone adhesive and suspended (solid) fentanyl alkaloid particles. In this process, the fentanyl was wetted with the 360 Medical Fluid and the resulting slurry combined with the heptane-solvated silicone adhesive to form a final suspension. This suspension was then cast onto the release liner and dried in an oven. The final step in this process was laminating the backing film onto the dried adhesive matrix.

The recrystallized formulation (246P118A) was produced by casting a blend of ethyl acetate-solvated adhesive and fentanyl. This blend was created by combining the fentanyl with the 360 Medical Fluid and the ethyl acetate-solvated silicone adhesive. All of the fentanyl dissolved in the blend. This blend was then cast onto the release liner and dried in an oven. The final step in this process was also laminating the backing film onto the dried adhesive matrix.

Table 6 shows the compositions of the two above formulations (which are theoretically identical in their dry form).

TABLE 6

| Lot Number | Description | Adhesive | 360 Medical Fluid (100 cSt) | Fentanyl | Residual Solvent (Trace quantities) |
|---|---|---|---|---|---|
| 246P114A | Laboratory Suspension Blend Laminate 9.5% Fentanyl | 84.0% w/w (7-4201) | 6.5% w/w | 9.5% w/w | Heptane |
| 246P118A | Laboratory Recrystallized Laminate 9.5% Fentanyl | 84.0% w/w (7-4202) | 6.5% w/w | 9.5% w/w | Ethyl Acetate |

FIG. 3 shows that the 7-day suspension-cast and recrystallized formulations were the same in terms of in vitro transdermal fentanyl delivery.

In another embodiment of the invention, FIG. 6 shows the cumulative in vitro transdermal delivery of fentanyl from a 7 day patch in accordance with the present invention. The lot R6J0014 was produced by casting a blend of heptane-solvated silicone adhesive(s) and suspended (solid) fentanyl alkaloid particles. A slurry was produced by mixing fentanyl directly with a portion of the heptane-solvated silicone adhesive(s). No silicone fluid was used. This slurry was then passed through a colloid mill to form a suspension. This suspension was then blended with the remaining heptane-solvated silicone adhesive to form the final (and more dilute) suspension that was cast onto a release liner and passed through ovens to drive off the heptane. The final step in this process was laminating a backing film onto the dried adhesive matrix. Table 7 shows the final (dry) composition of the adhesive matrix.

TABLE 7

| Component | w/w | g/m² |
|---|---|---|
| Fentanyl | 9.09% | 10 |
| Bio-PSA® 7-4201 Silicone Adhesive | 45.455% | 50 |
| Bio-PSA® 7-4301 Silicone Adhesive | 45.455% | 50 |

Table 8 shows a comparison of the (wet) composition of the suspension blend formulation and the final (dry) composition of the adhesive matrix shown in Table 7.

TABLE 8

| Component | Wet (w/w) | Dry (w/w) |
|---|---|---|
| Fentanyl | 6.54% | 9.09% |
| Bio-PSA® 7-4201 Silicone Adhesive | 46.73% | 45.455% |
| Bio-PSA® 7-4301 Silicone Adhesive | 46.73% | 45.455% |

Table 9 also shows a comparison of the (wet) composition of a suspension blend formulation and the final (dry) composition of an adhesive matrix, according to another embodiment in which no silicone fluid was used.

TABLE 9

| Component | Wet (w/w) | Dry (w/w) |
|---|---|---|
| Fentanyl | 6.85% | 9.5% |
| Bio-PSA® 7-4201 Silicone Adhesive | 46.58% | 45.25% |

TABLE 9-continued

| Component | Wet (w/w) | Dry (w/w) |
|---|---|---|
| Bio-PSA® 7-4301 Silicone Adhesive | 46.58% | 45.25% |

The ratio of adhesives used together may be adjusted without undue effort to improve adhesive properties, if necessary or desired.

Rate of Release of Fentanyl from Recrystallized vs. Suspension-Cast Laminates

FIG. 4 shows the rate of fentanyl release for the two lots R6J0001 and 246P110C tested for in vitro transdermal delivery.

FIG. 5 shows the rate of fentanyl release for lots 246114A and 246P118A tested for in vitro transdermal delivery.

FIG. 7 shows the rate of release for lot R6J0014 tested for in vitro transdermal delivery.

The above results show that the recrystallized laminates (246P110C and 246P118A) release fentanyl much faster than suspension-cast laminates (R6J0001, 246P114A and R6J0014) in accordance with the invention, i.e., more than 80% of the fentanyl is released within the first hour from the recrystallized laminates. The above differences may be due to fentanyl in the recrystallized laminates crystallizing at the release liner surface, which also may explain why the recrystallized laminates had no measurable tack, as shown below.

In contrast, in the suspension-cast laminates, fentanyl crystals were found to be evenly distributed throughout the matrix, rather than only at the release liner surface.

Polyken Probe Tack of Recrystallized and Suspension-Cast Laminates

The suspension-cast fentanyl laminates were also found to possess superior adhesive properties, as compared with the solution-cast laminates. As a result, more thorough measurements of Polyken probe tack were collected to quantitate any differences between the two processes (suspension-cast vs. solution-cast). Table 10 summarizes the results of the tack testing on these laminates.

TABLE 10

| Formulation | Process | Lot # | Tack (g/cm²) |
|---|---|---|---|
| (4% fentanyl) | Suspension-cast | R6J0001 | 2335 (n = 4) |
| (4% fentanyl) | Recrystallized | 246p110C | 0 (no adhesion to probe) |
| (9.5% fentanyl) | Suspension-cast | 246p114A | 1499 (n = 6) |
| (9.5% fentanyl) | Recrystallized | 246p118A | 0 (no adhesion to probe) |

Table 10 shows that the solution-cast laminates have no measurable tack compared to the suspension-cast laminates.

Table 11 shows the results of tack testing for the 7 day patch (lot R6J0014)

TABLE 11

| Polyken Probe Tack (g/cm²) | 1451 ± 280 |
|---|---|

Photomicrographs were taken to compare qualitative observations of laminates produced from either solution blends or suspension blends.

The overall composition of laminate pairs produced from solution and suspension blends was the same, the only difference being the solvent used to solvate the adhesive blend. As the solvent was removed from the solution blends, the fentanyl crystallized.

In the suspension blend composition (R6J0001), fentanyl particles were more or less round and about 10 to 20 µm in diameter. Also present in the laminates are some agglomerates (about 30 to 60 µm in diameter), but very few single (rod-shaped) crystals.

In the solution blend composition (246p110c), very small crystals appeared throughout the laminate (too small to accurately measure their size). Clearer, low-density spots were visible to the naked eye. Under the microscope, these spots were found to have a relatively large crystal-agglomerate in the middle (~100 µm) surrounded by a crystal-free area. It was hypothesized that a large, low-energy crystal grew at the expense of the surrounding crystals. About 4-8 such agglomerates were seen in each 10 cm² laminate sample. Therefore, the solution blend tended to produce a laminate containing larger, discrete crystalline particles while the suspension blend produced a laminate with smaller, more evenly dispersed particles.

Two additional suspension blend and solution blend compositions were tested and compared. The overall composition of the laminates produced from the solution and suspension blends also was the same, the only difference being the solvent used to solvate the adhesive. As above, removal of the solvent from the solution blend caused the fentanyl to crystallize.

In the 7-day suspension blend composition (246p114A), the appearance was similar to the analogous 3-day suspension laminate above (R6J0001). In particular, most of the fentanyl particles were round in shape with a few rod-shaped crystals at the adhesive-release liner interface. Particle and agglomerate sizes also were similar to those in the 3-day suspension-cast laminate, although many more agglomerates were observed (as expected at a significantly higher drug load).

In the recrystallized 7-day blend composition (246p118A), the crystal shape and size was similar to the analogous 3-day solution-cast laminate (246p110C). However, as expected, many more agglomerates were observed in the 7-day laminates than in the 3-day laminate.

Devices made in accordance with the present invention are useful for inducing analgesia and sedation. Specific uses include the management of chronic pain in patients who require opioid analgesia for pain, such as for relief of acute postoperative and chronic cancer pain. Other possible uses include treatment of other chronic body pain, such as back pain and arthritis pain.

The invention is further illustrated by the following examples, which are not intended to be limiting.

EXAMPLE 1

Fentanyl free base (0.0245 kg) is uniformly dispersed in 360 Medical Fluid, 100 cSt (0.061 kg), in a glass jar with the help of a Ultra-Turrax T8 dispersing unit for 20 minutes. This premix is added slowly to heptane-solvated BIO-PSA® 7-4201 (0.751 kg), 70% w/w solids content, with continuous mixing utilizing a Glass-Col mixer. This is mixed for 20 minutes. Using a Warner-Mathis KTF coater, the mixture is then coated onto a release liner (Scotchpak® 1022) and then dried at 78° C. for about 10 minutes to obtain a coat weight of 99.1 g/m². The dried film is then laminated onto a backing film (MediFlex® 1000). Patches of appropriate size are then die-cut from the laminate prior to analyses.

EXAMPLE 2

Fentanyl free base (3.20 g) and 360 Medical Fluid, 100 cSt (4.00 g) are added in a 4 ounce glass jar. To this jar half of the pre-weighed heptane-solvated BIO-PSA® 7-4201 (103.34 g), 70.45% w/w solids content, is added. This mix is then homogenized with the help of a dispersing unit (D7801, Dottingen, TYP-1020 L) for 3 minutes. To this mixture the remaining half of the heptane-solvated BIO-PSA® 7-4201 is added. This blend is mixed with a simple lab blender for 3 minutes. Using a fixed knife, the blend is then coated onto a release liner (ScotchPak™ 1022) and then dried at 75° C. for 10 minutes to obtain a coat weight of 90-100 g/m². The dried film is then laminated onto a backing film (Mediflex® 1000). Patches of appropriate size are then die-cut from the laminate prior to analysis.

EXAMPLE 3

Fentanyl free base (2.00 g) is homogenized in 360 Medical Fluid-100cSt (5.00 g) in a 4 ounce glass jar with the help of a dispersing unit (D7801, Dottingen, TYP-1020 L) for 3 minutes. To this premix heptane-solvated BIO-PSA® 7-4201 (61.43 g), 70% w/w solids content, is added. This blend is mixed with a simple lab blender for 3 minutes. Using a fixed knife, the blend is then coated onto a release liner (Scotch-Pak™ 1022) and then dried at room temperature for 5 minutes and 70° C. for 10 minutes to obtain a coat weight of 90-100 g/m². The dried film is then laminated onto a backing film (Mediflex® 1000). Patches of appropriate size are then die-cut from the laminate prior to analysis.

EXAMPLE 4

Fentanyl free base (2.00 g) and 360 Medical Fluid-100 cSt (1.63 g) are added in a 4 ounce glass jar. To this jar, half of the pre-weighed heptane-solvated BIO-PSA® 7-4201 (30.34 g), 70.45% w/w solids content, is added. This mix is then homogenized with the help of a dispersing unit (D7801, Dottingen, TYP-1020 L) for 3 minutes. To this mixture the remaining half of the heptane-solvated BIO-PSA® 7-4201 is added. This blend is mixed with a simple lab blender for 3 minutes. Using a fixed knife, the blend is then coated onto a release liner (ScotchPak™ 1022) and then dried at 75° C. for 10 minutes to obtain a coat weight of 90-100 g/m². The dried film then is laminated onto a backing film (Mediflex® 1000). Patches of appropriate size are then die-cut from the laminate prior to analysis.

EXAMPLE 5

Fentanyl free base (3.17 g), 360 Medical Fluid-100 cSt (2.17 g), and heptane-solvated BIO-PSA® 7-4201 (39.74 g), 70.45% w/w solids content, are added in a 4 ounce glass jar. This mix then is homogenized with the help of a dispersing unit (D7801, Dottingen, TYP-1020 L) for 3 minutes to fully disperse fentanyl. Using a fixed knife, the blend is then coated onto a release liner (ScotchPak™ 1022) and then dried at 72° C. for 10 minutes to obtain a coat weight of 90-100 g/m². The dried film is then laminated onto a backing film (Mediflex® 1000). Patches of appropriate size are then die-cut prior to analysis.

EXAMPLE 6

Fentanyl free base (3.17 g), heptane-solvated BIO-PSA® 7-4201 [21.41 g, 70.45% w/w solids content], and heptane-solvated BIO-PSA® 7-4301 [19.85 g, 76.00% w/w solids content], are added in a 4 ounce glass jar. This mix is then homogenized with the help of a dispersing unit (D7801, Dottingen, TYP-1020 L) for 3 minutes to fully disperse fentanyl. Using a fixed knife, the blend is then coated onto a release liner (ScotchPak™ 1022) and then dried at 72° C. for 10 minutes to obtain a coat weight of 110 g/m². The dried film then is laminated onto a backing film (Mediflex® 1000). Patches of appropriate size then are die-cut prior to analysis.

EXAMPLE 7

Fentanyl free base (12.73 g) and heptane-solvated BIO-PSA® 7-4301 (181.82 g, 70.0% w/w solids content) were added to an 8 oz glass jar. This mixture was then homogenized with a dispersing unit (Vertishear, 20 mm diameter shaft) for 3 minutes to fully disperse the fentanyl particles. Using a doctor blade, the blend was coated onto a release liner (ScotchPak™ 1022) and dried at 72° C. for 10 minutes to obtain a coat weight of 100-110 g/m². The dried film was then laminated onto a backing film (Mediflex® 1000). Patches of appropriate size were then die-cut from the finished laminate to form the delivery systems.

The publications and other materials used herein to illuminate the background of the invention, as well as provide additional details respecting the practice of the invention, are incorporated herein by reference to the same extent as if they were specifically and individually indicated to be incorporated by reference.

While the invention has been disclosed by reference to the details of preferred embodiments of the invention, it is to be understood that the disclosure is intended in an illustrative rather than a limiting sense, as it is contemplated that modifications will readily occur to those skilled in the art, within the spirit of the invention and the scope of the appended claims.

What is claimed is:

1. A method for making a monolithic suspension-blend transdermal patch comprising: (a) contacting an inner layer of a backing layer having inner and outer surfaces and being substantially impervious to fentanyl with first surface of a first adhesive layer, the adhesive layer comprising a uniform suspension of a 72 to 168 hour period therapeutically-effective amount of fentanyl particles suspended in a silicone adhesive, the fentanyl particles consisting essentially of non-recrystallized fentanyl, the silicone adhesive comprising heptane solvent fully-solvated silicone adhesive from which the heptane solvent is substantially removed, the heptane solvated adhesive being incapable of dissolving greater than 1% w/w of said fentanyl particles; and (b) contacting a second surface of the adhesive layer with a removable release liner; wherein the fentanyl load of the suspension-based patch ranges from about 1 to about 15% w/w (dry weight) based upon the weight of the fentanyl silicone adhesive suspension; whereby when the suspension-blend patch is administered to a subject in need thereof, the adhesive layer delivers from about 5 μg/hr to about 250 μg/hr of the fentanyl to the subject for the period.

* * * * *